United States Patent
Berthe et al.

(10) Patent No.: US 10,590,058 B2
(45) Date of Patent: Mar. 17, 2020

(54) HYDROBROMINATION METHOD

(71) Applicant: Arkema France, Colombes (FR)

(72) Inventors: Bernard Berthe, Lons (FR); Bernard Pees, Allauch (FR); Philippe Annoot, Saint Aubin le Guichard (FR); Jean-Luc Dubois, Millery (FR); Ornella Zovi, Le Theil-nolent (FR)

(73) Assignee: ARKEMA FRANCE, Colombes (FR)

( * ) Notice: Subject to any disclaimer, the term of this patent is extended or adjusted under 35 U.S.C. 154(b) by 208 days.

(21) Appl. No.: 14/909,775

(22) PCT Filed: Aug. 7, 2014

(86) PCT No.: PCT/FR2014/052062
§ 371 (c)(1),
(2) Date: Feb. 3, 2016

(87) PCT Pub. No.: WO2015/019028
PCT Pub. Date: Feb. 12, 2015

(65) Prior Publication Data
US 2016/0185705 A1 Jun. 30, 2016

(30) Foreign Application Priority Data
Aug. 9, 2013 (FR) ..................... 13 57928

(51) Int. Cl.
*C07C 51/363* (2006.01)
*C07C 227/08* (2006.01)
*C08G 69/08* (2006.01)

(52) U.S. Cl.
CPC .......... *C07C 51/363* (2013.01); *C07C 227/08* (2013.01); *C08G 69/08* (2013.01); *Y02P 20/582* (2015.11)

(58) Field of Classification Search
CPC .. C08F 8/20; C08K 5/02; C10G 29/26; C07C 227/08; C07C 51/363
See application file for complete search history.

(56) References Cited

U.S. PATENT DOCUMENTS

| | | | | |
|---|---|---|---|---|
| 3,396,204 A | * | 8/1968 | McCarty | B01J 10/02 204/158.12 |
| 3,699,179 A | * | 10/1972 | Boyle | C07C 17/08 570/241 |
| 2009/0054709 A1 | | 2/2009 | Torres et al. | |

FOREIGN PATENT DOCUMENTS

| | | |
|---|---|---|
| CN | 1100030 C | 6/1999 |
| CN | 102 531 879 A | 7/2012 |
| FR | 951 932 A | 11/1949 |
| WO | WO 2007/121228 A2 | 10/2007 |

OTHER PUBLICATIONS

International Search Report (PCT/ISA/210) dated Jan. 8, 2015, by the French Patent Office as the International Searching Authority for International Application No. PCT/FR2014/052062.
Notification of Transmittal of Translation of the International Preliminary Report on Patentability (Forms PCT/IB/338 and PCT/IB/373) and the Written Opinion of the International Searching Authority (Form PCT/ISA/237) dated Feb. 18, 2016, by the International Bureau of WIPO in corresponding International Application No. PCT/FR2014/052062. ( 9 pages).

* cited by examiner

*Primary Examiner* — Gregory Listvoyb
(74) *Attorney, Agent, or Firm* — Thomas F. Roland

(57) ABSTRACT

A process for synthesizing a product of formula Br—$(CH_2)_n$—R by hydrobromination, by reacting: a reagent of formula (I) R1-CH=CH—R2 in which R1 and R2, identical or different, are chosen from H or an alkyl radical comprising 1 to 30 carbon atoms, which is saturated or unsaturated, linear or branched, functionalized or non-functionalized, with a molar excess of HBr relative to the reagent of formula (I), in the presence of a radical initiator, and optionally in the presence of at least one solvent, said process including a step A of mixing at least reagent I and the HBr, each of the latter arriving in the form of a flow of liquid into a mixing device dA.

24 Claims, No Drawings

HYDROBROMINATION METHOD

The invention relates to a continuous process for producing a compound of formula R1-CHBr—CH$_2$—R2 (preferably Br—(CH$_2$)$_2$—R2, for example Br—(CH$_2$)$_2$—R'—COOH) by hydrobromination from a compound I of formula: R1-CH=CH—R2 (preferably CH$_2$=CH—R, for example CH$_2$=CH—R'—COOH), in which R1 and R2, which may be identical or different, are each independently H or an alkyl radical comprising from 1 to 30 carbon atoms, preferably from 6 to 15 carbon atoms, which are saturated or unsaturated (alkene, alkyne), linear or branched, and functionalized (in particular with at least one acid, ester, nitrile, alcohol and/or aldehyde function) or non-functionalized.

The present invention relates quite particularly to a novel process for synthesizing α,ω-bromoalkanoic acid (hereinafter ω-bromo acid) capable of being used in the polymer industry, in particular the polyamide industry, said process comprising a step of radical hydrobromination of an ω-unsaturated acid in the presence of HBr, the latter arriving to the reaction in liquid form (i.e. either liquefied under its saturated vapor pressure or in solution in a solvent or solvent mixture).

Among the ω-bromo acids, 11-bromoundecanoic acid (also referred to as 11-Bromo acid) has many applications in industry, in particular owing to the presence of its two bromide and acid reactive functions, which are capable of reacting. 11-Bromo acid is the starting product for a large number of industrial chemical reactions, in particular for the production of 11-aminoundecanoic acid, used as a monomer for synthesizing polyamide 11.

PRIOR ART

Currently, two hydrobromination processes are described in the literature, using a column device or tower for carrying out the hydrobromination reaction. The process described in patent document FR951932 uses dissolution of undecylenic acid in a mixture of benzene and toluene; the mixture, precooled to −10° C., flows in a tower packed with Raschig rings. A gas mixture consisting of hydrobromic acid and air is introduced into the tower in countercurrent mode. The reaction takes place in a small space in the column. In this zone, the temperature rises to 30° C. The 11-bromoundecanoic acid yield is, under these conditions, included in the range of from 95% to 97%.

Patent document CN1100030C describes a hydrobromination process in 2 steps, absorption and reaction, using toluene as solvent for the undecylenic acid, in the presence of a catalyst, in a device using successively several large-capacity (volume) columns, into which HBr is introduced in gas form.

The radical hydrobromination reaction is preferably carried out in nonpolar or apolar solvents i.e. solvents with a low dipole moment (since polar solvents, with a high dipole moment, capture free radicals) and with reagents which are as pure as possible (since impurities destroy free radicals).

In order to be able to solubilize the HBr and the other reagents at the hydrobromination reaction temperature, the prior art processes generally use solvents such as benzene, toluene, methylcyclohexane, trifluorotoluene ("BTF"), isooctane or heptane. Aromatic solvents such as benzene, toluene or xylene, and also halogenated solvents such as monochlorobenzene, are generally described as "good solvents". The term "good solvent" is intended to mean a solvent which allows miscibility and solubility of the reagents and of the products of the hydrobromination reaction at the hydrobromination reaction temperature, and which thus provides the system with better reactivity. Miscibility usually denotes the capacity of various liquids to mix together. If the mixture obtained is homogeneous, the liquids are described as miscible for the purposes of the invention. The solubility of an ionic or molecular compound, called solute, is the maximum concentration (in moles per liter) of this compound that can be dissolved or dissociated in a solvent, at a given temperature.

By allowing total solubility of the reagents and products, a good solvent also prevents blockages in the equipment. Conversely, solvents such as cyclohexane, methylcyclohexane or heptane are generally categorized as "poor solvents" in this type of hydrobromination process.

In the future, for health, safety and environmental reasons, the use of aromatic and/or halogenated solvents should be avoided. Furthermore, the abovementioned good solvents have another drawback in that they are generally difficult to remove from the system by evaporation.

The objective of the present invention is therefore to provide a process which makes it possible to equal, or even to exceed, the yield obtained with the current process(es), using all types of solvents, including "poor solvents" which are neither aromatic or halogenated and which solubilize the reagents with difficulty in the current processes.

Moreover, the current hydrobromination processes with a packed column make it obligatory, in order to recycle the HBr, to use a system of stripping type which leads to a strong degradation of the color of the brominated product, i.e. results in a strongly brown-colored product.

The objective of the present invention is also to find a continuous industrial process which makes it possible to control and optimize the various parameters of the hydrobromination reaction: mixing of the reagents, reaction temperature, residence time, amount of solvent, reagent flow rate, reagent and/or solvent recycling, and which makes it possible to achieve the imposed specifications, in particular in terms of degree of conversion and yield, and to improve the quality of the product obtained.

The applicant has now found such a continuous hydrobromination process characterized by a particular flow system and a particular residence time making it possible to solve the abovementioned problem.

A subject of the present invention is therefore a process for synthesizing a product of formula Br—(CH2)$_n$—R2 by hydrobromination by reacting:

a reagent of formula (I) R1-CH=CH—R2 in which R1 and R2, which may be identical or different, are chosen from H or an alkyl radical comprising from 1 to 30 carbon atoms, preferably from 1 to 20 carbon atoms, preferably from 6 to 15 carbon atoms, which is saturated or unsaturated, linear or branched, and functionalized or non-functionalized, with a molar excess of HBr relative to the reagent of formula (I), in the presence of a radical initiator, and optionally in the presence of at least one solvent, said process being characterized in that it comprises a step A of mixing at least the reagent I and the HBr, each of the latter arriving respectively in the form of a liquid stream in a mixing device dA.

The reagent I (or compound I) used is in liquid form, either melted at a temperature above its melting point, or dissolved in a solvent. The compound or reagent I has the formula R1-CH=CH—R2, preferably CH$_2$=CH—R2. Mention may, for example, be made of CH$_2$=CH—R'—COOH in which R' is an alkyl radical comprising from 1 to 29 carbon atoms, preferably from 1 to 19 carbon atoms, preferably from 6 to 14 carbon atoms, which is saturated or unsaturated (alkene, alkyne), linear or branched, and functionalized (in particular with at least one acid, ester, nitrile, alcohol and/or aldehyde function) or non-functionalized. Thus, the present invention is directed in particular toward the production of Br—$(CH_2)_2$—R2 products, for example Br—$(CH_2)_2$—R'—COOH.

The HBr used in the process of the invention is in liquid form, in particular liquefied under its saturated vapor pressure or in solution in a solvent or solvent mixture as described below. Mention may in particular be made of the HBr sold by L'Air Liquide or by Air Products.

The radical initiator is chosen from air, $O_2$, a peroxide, a diazo compound, or any other radical generator, such as UV radiation. According to one particular embodiment of the process of the invention, the radical initiator preferably comprises oxygen, preferred for the ease with which it can be industrially processed, its stability, and its low cost compared with the other types of initiators. The radical initiator can be added upstream of the device dA, for example added to the HBr stream, or else directly into the mixing device dA, or else downstream of the device dA, i.e. into the stream comprising the mixture of HBr and of reagent I leaving dA, or else at several places among those mentioned above.

The hydrobromination according to the process of the invention is carried out in a homogeneous liquid medium, or else in liquid-gas phase, in particular in the case where the radical initiator is injected in gas form directly into the device dA, or else downstream of dA. Preferably, the hydrobromination is carried out in a homogeneous liquid medium.

In the case where a solvent is used, a good solvent for both the HBr and the reagent 1 dissolved is preferably used. The solvent used may be polar or apolar, preferably apolar.

When a solvent is used in the process of the invention, said solvent is preferably chosen from: benzene, fluorobenzene, chlorobenzene, toluene, α,α,α-trifluorotoluene, ethylbenzene, xylenes, cyclohexane, methylcyclohexane, methylcyclopentane, n-hexane, 2-methylhexane, 3-methylhexane, n-heptane, isooctane, tetrachloroethylene, 1,1,1-trichloroethane, dibromomethane, trichloromethane, tetrachloromethane, 1,1,1-bromopropane, dimethyl carbonate, tetrahydrofuran (THF), 1,4-dioxane, 2-methyltetrahydrofuran, tetrahydropyran (THP), 1-propoxypropane, 1-ethoxybutane, 2-isopropoxypropane and acetonitrile, and mixtures thereof.

Preferably, the solvent comprises at least one of the following solvents: benzene, fluorobenzene, chlorobenzene, trifluorotoluene ("BTF"), ethylbenzene, toluene, xylene, cyclohexane, methylcyclohexane, heptane, isooctane, 1,1,1-trichloroethane and dibromomethane, and mixtures thereof.

Preferably, the process of the invention uses at least one solvent chosen from aliphatic solvents, such as cyclohexane, methylcyclohexane or heptane, and mixtures thereof, optionally as a mixture with at least one other solvent chosen from aromatic solvents such as benzene, toluene or xylene, or halogenated solvents such as monochlorobenzene, and mixtures thereof.

Advantageously, the optional solvents arrive in the mixing device at a temperature included in the range of from −50° C. to 20° C., preferably from −40° C. to 10° C., preferably from −30° C. to 0° C., preferably from −30° C. to −10° C. Indeed, in order to have HBr and the reagent I soluble in the solvent, the temperature at which the solvent is used is preferably between the highest temperature of crystallization of the reagents and the limiting temperature of the anti-Markovnikov reaction, i.e. in the range of from −50° C. to 20° C. The device dA may also comprise a cooling system in order to compensate for the exothermicity of the hydrobromination reaction, and to promote the anti-Markovnikov reaction.

Advantageously, a turbulent flow system prevails in the mixing device dA. At the end of this step A a degree of conversion included in the range of from 10% to 100% is reached. Advantageously, the turbulent flow system of step A is characterized by a Reynolds number >1800, preferably >2000, preferably >3000. The turbulent system is regulated in a known manner by those skilled in the art, by adjusting the entering P induced by the flow rate and the cross section of the pipes (tube, proportioning) arriving in the mixing device dA, and by forcing the diffusion of the streams in the device, this diffusion being linked in particular to the volume of the mixing device dA.

By virtue of the very good initial instantaneous mixing allowed by step A, which optimizes the meeting of the reagents, the process of the invention is faster than the conventional processes using a packed-column reactor.

Advantageously, the residence time of step A is less than 10 minutes, preferably included in the range of from 0.01 second to 10 minutes, preferably included in the range of from 0.01 second to 5 minutes, preferably included in the range of from 0.01 second to 1 minute, preferably from 0.01 to 30 seconds, preferably from 0.01 to 10 seconds, preferably from 0.2 to 5 seconds, preferably from 0.2 to 2.5 seconds, preferably from 0.2 to 2 seconds, preferably from 0.2 to 1 s.

Advantageously, the residence time of step A is less than the reaction time.

Initiating the reaction very rapidly and forcing the reagents to meet by means of the device dA allows more intimate and faster mixing thereof, and therefore reaction thereof, and then the reaction propagates spontaneously. The process of the invention makes it possible to use "poor solvents" as defined above, and as demonstrated in the examples hereinafter.

According to one particular embodiment, the degree of conversion at the end of step A is included in the range of from 10% to 99.99%, preferably from 10% to 90%. Indeed, according to one particular embodiment, the process of the invention also comprises a step B of spontaneous continuation (and/or finishing) of the reaction in a device dB in which a transient or laminar flow system prevails, so as to reach, at the end of this step, a degree of conversion of greater than 90%, preferably of at least 95%.

Preferably, the transient or laminar flow system of step B is characterized by a Reynolds number <3000, preferably <2000, preferably <1800, preferably <1300.

Advantageously, the residence time in the devices dA and dB are such that the degree of conversion at the end of step A is included in the range of from 10% to 90%, while the degree of conversion at the end of step B is included in the range of from 90% to 100%.

According to one particular embodiment of the process of the invention, the compound of formula (I), and the optional solvent arrive in the mixing device dA in a stream Fa, while the HBr, the optional solvent and the initiator arrive in the mixing device dA in a second stream Fb during step A, the ratio of the streams Fa and Fb being kept substantially constant, and the stream Fr resulting from the mixing of the streams Fa and Fb is directed from the outlet of the mixing device dA into the reaction finishing device dB.

According to another particular embodiment of the process of the invention, the compound of formula (I), the initiator and the optional solvent arrive in the mixing device dA in a stream Fa, while the HBr and the optional solvent arrive in the mixing device dA in a second stream Fb during step A, the ratio of the streams Fa and Fb being kept substantially constant, and the stream Fr resulting from the mixing of the streams Fa and Fb is directed from the outlet of the mixing device dA into the reaction finishing device dB.

Advantageously, the device dA comprises a device of about one decimeter, one centimeter, one millimeter or one micrometer, such as a "microdevice", in particular a microreactor or micromixer.

Advantageously, the mixing device dA used in the process of the present invention comprises at least one reactor and/or at least one mixer, each having:
- a small total internal volume, generally included in the range of from 1 microliter to 200 liters, preferably from 1 microliter to 100 liters, preferably from 1 microliter to 10 liters, preferably from 1 microliter to 1 liter, preferably from 1 microliter to 500 milliliters, preferably from 0.1 ml to 200 ml, preferably from 0.1 ml to 100 ml, and more preferably for the reactor from 10 to 60 ml;
- a value of the ratio between its internal surface area and its internal volume of greater than 50 $m^2 \, m^{-3}$, preferably greater than 500 $m^2 \, m^{-3}$, preferably greater than 1000 $m^2 \, m^{-3}$;
- a characteristic dimension, namely the shortest distance between two walls facing one another, included in the range of from 1 µm to 1 m, preferably 1 µm to 10 cm, preferably from 1 µm to 1 cm, preferably 0.5 mm to 5 mm and more preferably for microreactors from 1 to 3 mm.

The device dA can in particular comprise one or more "microdevice(s)", for example a set of microstructured reactor(s) and/or mixer(s) mounted in series or in parallel.

The first objective of the mixing device dA is to bring into contact two fluids, the one containing the reagent I and the one containing the HBr, in order to rapidly homogenize them, and to promote the transfer of material and therefore the hydrobromination reaction. The geometry and the type of bringing into contact of the fluids define the performance level of the apparatus. For mixing miscible fluids, the performance level of the mixing device dA is directly linked to the characteristic distance between the species, generally determined by the geometry of the device dA. Coupled with the operating conditions of the process according to the invention, they control the physical characteristics of the mixture. Enormous possibilities exist and depend on the device production technologies retained. By way of example, the most common modes for bringing fluids into contact are:
- T-type or Y-type contacting of two streams. If the dimensions of the (micro)channel are small enough, the process of mixing by diffusion may be rapid since the characteristic distance of the system is very small. However, the flow rate passing through must be high enough to induce non-stationnary effects in the flow;
- multi-lamination by introduction of multiple streams of two components, often in an interdigital manner. The mixing time is therefore dependent on the width of each fluid filament, determined by the size of the (micro) channels. In the case where the width of each channel is relatively large (>100 mm), since mixing by molecular diffusion is not very effective, the mixing time can be decreased by coupling the multi-lamination with the hydrodynamic convergence mechanism;
- hydrodynamic convergence by decreasing the diffusion distance, normal to the direction of flow. By abruptly or gradually narrowing the width of the (micro)channel, the hydrodynamic convergence mechanism makes it possible to reduce the mixing time by forcing the fluid filaments through a narrower orifice, thereby reducing the characteristic distance for the diffusion;
- division and recombination of streams. The fluids undergo phases of restriction, cutting up and recombination, in order to increase the surface of contact between the lamellae of fluid and to decrease the thicknesses thereof. The flows generated with this mechanism often have turbulent characteristics which allow rapid and efficient mixing;
- mechanisms of chaotic mixing when a periodic disruption is applied to the flow.

By way of examples of devices that can be used in the process of the invention, mention may also be made of Venturi-effect mixers.

The turbulent flow promoted in the device dA used in the process of the invention is favorable to mixing since it makes it possible to separate, at an exponential rate, two infinitesimal amounts of fluids initially very close and to thus increase the interface between the species. It can be generated by a three-dimensional and periodic geometry, or during a disruption which is periodic in time, created by an external source (for example the periodic injection of a stream normal to the main flow).

Devices that can be used for the process of the invention may be the equipment sold by IMM (for example, Star Laminator, falling-film reactors), Ehrfeld BTS (for example, the Impinging Jet microjet mixer, or the MiProwa reactor), LTF (Tangential flow), Mikroglas Chemtech, Corning (glass microreactors), Zeton, Cytos, Velocys, Venturi mixers, for example of B3 type; for miscible-fluid mixing applications. The glasses that can be used to produce these microreactors are all types of glass, such as borosilicate glasses (Pyrex®, for example), soda-lime glasses, lead glasses, silica glasses or vitroceramics. Any material other than glass can of course be chosen for the device, provided that it is compatible with the reaction medium.

Advantageously, step A of mixing the reagents is carried out under flow-rate and pressure conditions such that, within the mixing device dA, the circulating reactive fluids have short characteristic times, namely a residence time of less than 10 minutes, preferably included in the range of from 0.01 second to 5 minutes, preferably included in the range of from 0.01 second to 1 minute, preferably from 0.01 to 30 seconds, preferably from 0.01 to 10 seconds, preferably from 0.2 to 5 seconds, preferably from 0.2 to 2.5 seconds, preferably from 0.2 to 2 seconds, preferably from 0.2 to 1 s.

Preferably, during step A, the temperature of entry of the compound I into the mixing device dA is included in the range of from 0 to 100° C., preferably from 0 to 80° C., it being understood that, if the compound I enters alone (without solvent), it is at a temperature above the melting point Mp of the compound I, preferably above Mp+30° C., preferably above Mp+50° C., whereas, if it enters diluted in a solvent, said mixture of compound I and solvent enters the device dA at a temperature included in the range of from 0 to 50° C.

Advantageously, during step A, the HBr entry temperature, when it enters diluted in a solvent, is included in the range of from −50° C. to 50° C., preferably from −50° C. to 0° C.

Preferably, the HBr reagent is in an excess of at least 0.1 mol %, preferably from 0.1 mol % to 100 mol %, preferably from 0.1 mol % to 99.9 mol %, preferably in an excess included in the range of from 1 mol % to 50 mol % relative to the reagent of formula (I).

Advantageously, the HBr/optional total solvent weight ratio is included in the range of from 1% to 30%, preferably from 2% to 25%, preferably from 2% to 20%, preferably from 4% to 15%.

Advantageously, the reagent I/total solvent weight ratio, when a solvent is used, is included in the range of from 1% to 80%, preferably from 1% to 70%, preferably from 1% to 60%, preferably from 1% to 50%, preferably from 1% to 40%, preferably from 2% to 25%, preferably from 4% to 20%. An important advantage of the process according to the invention is that it makes it possible to use less solvent than the prior art processes.

The radical initiator/HBr ratio is preferably included in the range of from 0.01% to 80%, preferably from 0.05% to 70%, preferably from 0.1% to 60%, or even from 0.1% to 50%.

Preferably, the hydrobromination is carried out at a temperature included in the range of from −50 to 50° C., preferably from −20 to 20° C. Advantageously, the hydrobromination reaction is carried out at least partially (i.e. over at least a part of the reaction) in adiabatic mode. The process of the invention thus enables a considerable energy saving to be made.

Preferably, at the end of step A, the temperature at which the product leaves the device dA is above the crystallization temperature of the product, preferably included in the range of from −50° C. to 50° C., preferably from −40° C. to 40° C., preferably from −30° C. to 30° C., preferably from −30° C. to 20° C.

Preferably, the temperature at which the product leaves the device dA must not exceed 50° C. in order to promote a Karash reaction (i.e. to limit or prevent the Markovnikov reaction), and thus to obtain for example 11-bromoundecanoic acid instead of 10-bromoundecanoic acid. However, conversely, it is preferable for the temperature at which the product leaves the device dA not to be below −50° C. since there is a risk of the exiting stream crystallizing or setting or blocking.

Advantageously, the process of the invention does not use hyrobromination catalyst. Of course, it is nevertheless possible to use a catalyst, chosen from the catalysts known for this type of reaction.

At the end of the mixing step A and/or at the end of the optional finishing step B, a mixture of product, optional solvent and residual HBr is collected, it being possible for said process to also comprise a step C of separating and recovering the product, and the optional recycling of the HBr and/or of the solvent to the mixing device dA.

A subject of the present invention is also the production of 11-bromoundecanoic acid from undecylenic acid, by means of the process as defined above. Advantageously, the process of the invention also comprises an ammonolysis (or amination) step so as to form a compound of formula $NH_2-(CH_2)_n-R_2$, such as 11-aminoundecanoic acid. Advantageously, the process of the invention also comprises a step of synthesis of polyamide by polymerization of the compound of formula $NH_2-(CH_2)_n-R_2$.

EXAMPLES

The process of the invention is illustrated by the examples hereinafter.

Examples of Tests 1 to 4 (According to the Invention)

In the following examples, various solvents indicated in table 1 are tested. In these examples, the procedure is the same as that described for test 4 of table 1, using a micromixer.

Description of the micromixer: two streams are introduced according to four side jets Ja (2 jets opposite one another) and Jb (2 jets opposite one another), Ja being the solution of C11 (optionally molten) and Jb the solvent containing the HBr. The jets are each inclined by an angle of 90° relative to the vertical formed by these four jets. The mixing chamber has a volume of 0.32 ml.

Test 4 (according to the invention): A solution is prepared with 5.03 g of gaseous hydrobromic acid in 38.5 g of methylcyclohexane, by sending a stream of HBr into the solvent cooled to −20° C. In parallel, a solution is prepared with 352 g of undecylenic acid in 462 g of methylcyclohexane, through which a stream of oxygen is passed. The latter solution is maintained at 20° C. The two solutions are then sent (HBr/MeCHx flow rate=50 ml/min, C11/MeCHx flow rate=25 ml/min) to a micromixer which enables intimate mixing of the two streams of liquid. The solution exiting this process is composed of 11-bromoundecanoic acid, methylcyclohexane and residual HBr. This solution is plunged into a container containing water in order to eliminate the residual HBr. The organic phase is washed three times with 500 ml of water and then evaporated under reduced pressure so as to remove the methylcyclohexane.

The results obtained are:
Conversion=99.9%
Yield=95.0%
Expression of the results:
The yield (or percentage of product P, in this case % Br11) is determined by the following formula:

$$\% P = \frac{\text{Surface of the product } P}{\text{Total surface}} \times 100$$

Surface=area or intensity of the peak of the chromatogram measured by gas chromatography (GC).

In the case of the undecylenic acid hydrobromination reaction, the following will particularly be determined:
the percentage of residual undecylenic acid (% C11)
the percentage of 10-bromoundecanoic acid (% Br10)
the percentage of 9-bromoundecanoic acid (% Br9)
the percentage of 11-hydroxyundecanoic acid (% C11-OH)
the percentage of 11-bromoundecanoic acid (% Br11).

The total surface in the above formula represents the sum of the peaks: residual C11, C11-OH, Br9, Br10, Br11 of the final reaction mixture. The degree of conversion C of the undecylenic acid is determined by the following formula:
C=100−% starting C11.

Comparatives of Tests 1 to 4 (Using a Column)

In the comparatives, various solvents indicated in table 1 are tested, but using the process and the device of the prior art (column), according to the following operating conditions described in the case of test 2 (comparative):

Test 2 (Comparative):
- the solvent is a 70/30 v/v cyclohexane/benzene mixture,
- 15% by weight of undecylenic acid ("C11") dissolved in the solvents,
- column regulated at 0° C. in the top part and 10° C. in the bottom part,
- C11/solvent entry temperature=−12.5° C.,
- C11/solvent flow rate=80 g/min,
- HBr flow rate=6.32 g/min, i.e. a molar excess of 20% relative to the C11,
- air flow rate=0.196 l/min,
- H$_2$ flow rate=0.184 l/min.
- Yield=95.0%.

Table 1 below compares tests 1 to 4 (various solvents) carried out with a column (comparative) or with a micromixer (according to the invention):

TABLE 1

| | Solvent | | | | 11-Bromo Yield | |
|---|---|---|---|---|---|---|
| | "Good solvent" | | "Poor solvent" | | | |
| Tests | Benzene | MCB (monochlorobenzene) | Cyclohexane | Methylcyclohexane | Comparatives (column) | Invention (Micromixer) |
| 1 | | 100% | | | 95.7% | 95.9% |
| 2 | 30% | | 70% | | 95.0% | 95.3% |
| 3 | | | 80% | 20% | 94.0% | 95.0% |
| 6 | | | | 100% | 93.6% | 95.0% |

As shown in the tests of table 1, when benzene is replaced with a "poor solvent" in the existing processes, 1% of 11-Bromo yield is lost (95% with benzene, 94% in a column with the best of the poor solvents). Surprisingly, in the process of the invention, the same poor solvent allows, on the contrary, a level of 11-Bromo yield which has been recovered (95%) or which is better (for the same hydrobromination reaction). Unexpectedly, the best gap (increase) in yield is observed in the case of the "poor solvents" with the process of the invention.

Example 7

In these tests, the micromixer was replaced by a Venturi mixer.

Description of the Venturi mixer: a glass Venturi 11 cm long is fed by two pipes with an internal diameter of 4 mm and an external diameter of 6 mm.

An 80/20 by volume cyclohexane/methylcyclohexane ("CHx/MeCHx") mixture is sent to an absorption column via a peristaltic pump at a flow rate of 150 ml/min. HBr gas is sent to the absorption column medium at a flow rate of 9.7 g/min, i.e. a molar excess of 11% relative to the C11. The pure C11 acid is sent, at 50° C., to the mixing device (Venturi mixer) at a flow rate of 19.9 g/min, representing a concentration by weight of 14.5% relative to the total solvent. The HBr-saturated organic solution is sent to the mixing device via a gear pump at a flow rate of 150 ml/min. The oxygen is injected into the circuit just after the gear pump with an injection system: capillary tube immersed in the liquid at a flow rate of 0.04 nl/min. The mixing device is followed by a PFA (perfluoroalkoxy) pipe with an internal diameter of 4 mm and a length of 4 m.

| Solvent flow rate ml/min | Oxygen flow rate nl/min | Pure C11 flow rate g/min | HBr flow rate g/min | T° C. column bottom | T° C. column bottom | % Conversion | % 11-Bromo |
|---|---|---|---|---|---|---|---|
| 150 | 0.040 | 19.9 | 9.7 | −20 | −17 | 99.94 | 95.00 |

The degree of conversion and the yield of 11-bromo, obtained with the Venturi mixer, are identical to those obtained with the micromixer.

Example 8

In this test, the micromixer was replaced with a simple glass T, "T-shaped mixer".

Description of the T-shaped mixer used: The glass T of 5 cm long is fed by two pipes with an internal diameter of 4 mm and an external diameter of 6 mm. These pipes form an angle of 90° between them.

The 80/20 by volume CHx/MeCHx mixture is sent to an absorption column via a peristaltic pump at a flow rate of 150 ml/min. HBr gas is sent to the absorption column medium at a flow rate of 9.7 g/min, i.e. a molar excess of 11% relative to the C11. The pure C11 acid is sent, at 50° C., to the T-mixer at a flow rate of 19.9 g/min, representing a concentration by weight of 14.5% relative to the total solvent. The HBr-saturated organic solution is sent to the T-mixing device via a gear pump at a flow rate of 150 ml/min. The oxygen is injected into the circuit just after the gear pump with the injection system: capillary tube immersed in the liquid at a flow rate of 0.04 nl/min. The mixing device is followed by a PFA pipe with an internal diameter of 4 mm and a length of 4 m.

| Solvent flow rate ml/min | Oxygen flow rate nl/min | Pure C11 flow rate g/min | HBr flow rate g/min | T° C. column bottom | T° C. Mixer entry | T° C. Coil exit | % conversion | % 11-Bromo |
|---|---|---|---|---|---|---|---|---|
| 150 | 0.040 | 19.9 | 9.7 | −20 | −7 | 26-27° C. | 99.95 | 94.80 |

The degree of conversion and the yield of 11-bromo, obtained with this T-mixer, are identical to those obtained with the micromixer.

The invention claimed is:

1. A process for synthesizing a product of formula R1-CHBr—CH$_2$—R2 by hydrobromination by reacting:
   a) a reagent of formula (I) R1-CH=CH—R2 in which R1 and R2, which may be identical or different, are chosen from H or an alkyl radical comprising from 1 to 30 carbon atoms, which is saturated or unsaturated, linear or branched, and functionalized or non-functionalized,
   b) with a molar excess of HBr relative to the reagent of formula (I),
   in the presence of a radical initiator,
   and optionally in the presence of at least one solvent, said process comprising a step A of mixing at least the reagent I and the HBr, each of the latter arriving respectively in the form of a liquid stream in a mixing device dA, wherein a turbulent flow system prevails, so as to reach, at the end of this step A, a degree of conversion included in the range of from 10% to 100%, and wherein the process further comprises a step B of spontaneous continuation of the reaction in a device dB in which a transient or laminar flow system prevails, so as to reach, at the end of this step, a degree of conversion of greater than 90%, wherein the residence times in the devices dA and dB are such that the degree of conversion at the end of step A is included in the range of from 10% to 90%, while the degree of conversion at the end of step B is included in the range of from 90% to 100%.

2. The process of claim 1, wherein the turbulent flow system of step A is characterized by a Reynolds number >1800.

3. The process of claim 1, wherein the residence time of step A is less than 10 minutes.

4. The process of claim 1, wherein the residence time of step A is less than the reaction time.

5. The process of claim 1, wherein the radical initiator is chosen from air, $O_2$, peroxide, a diazo compound, or a radical generator.

6. The process of claim 1, wherein the reagent (I) used is in liquid form, either melted at a temperature above its melting point, or dissolved in a solvent.

7. The process of claim 1, wherein the hydrobromination is carried out in a homogeneous liquid medium.

8. The process of claim 1, wherein the HBr used is in liquid form, liquefied under its saturated vapor pressure or in solution in a solvent.

9. The process of claim 1, wherein the solvent comprises at least one of the following solvents: benzene, fluorobenzene, chlorobenzene, trifluorotoluene ("BTF"), ethylbenzene, toluene, xylene, cyclohexane, methylcyclohexane, heptane, isooctane, 1,1,1-trichloroethane and dibromomethane, and mixtures thereof.

10. The process of claim 1, wherein the process uses at least one solvent chosen from aliphatic solvents, optionally as a mixture with at least one other solvent chosen from aromatic solvents, or halogenated solvents.

11. The process of claim 1, wherein the optional solvents arrive in the mixing device at a temperature included in the range of from −50° C. to 20° C.

12. The process of claim 1, wherein the compound of formula (I) and the optional solvent arrive in the mixing device dA in a stream Fa, while the HBr, the optional solvent and the initiator arrive in the mixing device dA in a second stream Fb during step A, the ratio of the streams Fa and Fb being kept substantially constant, and the stream Fr resulting from the mixing of the streams Fa and Fb is directed from the outlet of the mixing device dA into the reaction finishing device dB.

13. The process of claim 1, wherein the device dA comprises a device of about one decimeter, one centimeter, one millimeter or one micrometer.

14. The process as claimed in claim 1, wherein the device dA comprises at least one reactor and/or at least one mixer, each having:
a small total internal volume, generally included in the range of from 1 microliter to 200 liters,
a value of the ratio between its internal surface area and its internal volume of greater than 50 $m^2\ m^{-3}$,
a characteristic dimension, namely the shortest distance between two walls facing one another, included in the range of from 1 μm to 1 m.

15. The process of claim 1, wherein the step A of mixing at least the reagent I and the HBr is carried out under flow rate and pressure conditions such that, within the mixing device dA, the circulating reactive fluids have short characteristic times, namely a residence time of less than 10 minutes, preferably included in the range of from 0.01 second to 5 minutes.

16. The process of claim 1, wherein during step A, the temperature of entry of the compound I into the mixing device dA is included in the range of from 0 to 100° C., it being understood that, if the compound I enters alone, it is at a temperature above the melting point Mp of the compound I, whereas if it enters diluted in a solvent, said mixture of compound I and solvent enters dA at a temperature included in the range of from 0 to 50° C.

17. The process of claim 1, wherein during step A, the HBr entry, temperature, when it enters diluted in a solvent, is included in the range of from −50° C. to 50° C.

18. The process of claim 1, wherein the HBr reagent is in an excess of at least 0.1 mol % relative to the reagent of formula (I).

19. The process of claim 1, wherein the HBr/optional total solvent weight ratio is included in the range of from 1% to 30%.

20. The process of claim 1, wherein the reagent 1/optional total solvent weight ratio is included in the range of from 1% to 80%.

21. The process of claim 1, wherein the radical initiator/HBr ratio is included in the range of from 0.01% to 80%.

22. The process of claim 1, wherein the hydrobromination is carried out at a temperature included in the range of from −50 to 50° C.

23. The process of claim 1, wherein the hydrobromination reaction is carried out at least partially in adiabatic mode.

24. The process of claim 1, wherein at the end of step A, the temperature at which the product leaves the device dA is above the crystallization temperature of the product, preferably included in the range of from −50° C. to 50° C.

* * * * *